US012634151B2

(12) United States Patent
Principato et al.

(10) Patent No.: US 12,634,151 B2
(45) Date of Patent: May 19, 2026

(54) MANAGED MEMORY DEVICE WITH INTEGRATED RADIO-FREQUENCY IDENTIFICATION COMPONENT FOR CRYPTOGRAPHIC TRACKING

(71) Applicant: Micron Technology, Inc., Boise, ID (US)

(72) Inventors: Giuseppe Principato, Poing (DE); Francesco Lupo, Munich (DE)

(73) Assignee: Micron Technology, Inc., Boise, ID (US)

( * ) Notice: Subject to any disclaimer, the term of this patent is extended or adjusted under 35 U.S.C. 154(b) by 131 days.

(21) Appl. No.: 18/776,751

(22) Filed: Jul. 18, 2024

(65) Prior Publication Data

US 2026/0025280 A1    Jan. 22, 2026

(51) Int. Cl.
*H04L 29/06*        (2006.01)
*G16H 10/60*        (2018.01)
*H04L 9/08*        (2006.01)
*H04L 9/32*        (2006.01)

(52) U.S. Cl.
CPC ........... *H04L 9/3247* (2013.01); *G16H 10/60* (2018.01); *H04L 9/0825* (2013.01); *H04L 9/3278* (2013.01); *H04L 2209/805* (2013.01)

(58) Field of Classification Search
CPC ... H04L 9/3247; H04L 9/0825; H04L 9/3278; H04L 2209/805; G16H 10/60
See application file for complete search history.

(56) References Cited

U.S. PATENT DOCUMENTS

| | | | | |
|---|---|---|---|---|
| 10,073,955 | B2 * | 9/2018 | Ervin ..................... | A61J 7/0427 |
| 12,128,007 | B2 * | 10/2024 | Badik ................... | A61J 7/0076 |
| 2006/0089858 | A1 * | 4/2006 | Ling ...................... | G16H 40/67 |
| | | | | 705/2 |
| 2007/0192191 | A1 * | 8/2007 | Neal ................ | G07B 17/00435 |
| | | | | 705/14.26 |
| 2016/0314274 | A1 * | 10/2016 | Zieger ................. | H04L 63/0861 |
| 2017/0193191 | A1 * | 7/2017 | Blum ..................... | G16H 20/13 |
| 2022/0028515 | A1 * | 1/2022 | Amoyal .................. | G06F 21/31 |

* cited by examiner

*Primary Examiner* — Harunur Rashid
(74) *Attorney, Agent, or Firm* — Harrity & Harrity, LLP

(57) ABSTRACT

A memory device includes a radio-frequency identification (RFID) component configured to communicate with an external system for transmitting a device identifier to the external system and for receiving data from the external system; one or more memory dies configured to store the data; a communication interface configured to transmit a message that includes a digital signature and the device identifier for authenticating the memory device; and a secure memory controller configured to manage operations of the one or more memory dies. The secure memory controller is configured with a cryptographic function for generating the digital signature based on asymmetric encryption. The RFID component provides a trigger signal to the secure memory controller based on the RFID component being activated by the external system. The secure memory controller generates the digital signature, for being provided in the message, based on the secure memory controller receiving the trigger signal.

27 Claims, 4 Drawing Sheets

400 —►

410 — Activate an RFID component of a memory device

420 — Transmit a device identifier of the memory device to the verification system based on the RFID component being activated 430 — Transmit a trigger signal to a secure memory controller of the memory device based on the RFID component being activated 440 — Generate a digital signature based on a private key and the device identifier based on the secure memory controller receiving the trigger signal 450 — Transmit a message to the verification system, wherein the message includes the digital signature and the device identifier 460 — Look up a public key associated with the private key using the device identifier received from the RFID component, the public key being stored in a database of the verification system 470 — Authenticate the memory device based on the message received from the communication interface and the public key retrieved from the database

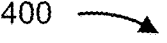

410 — Activate an RFID component of a memory device

420 — Transmit a device identifier of the memory device to the verification system based on the RFID component being activated 430 — Transmit a trigger signal to a secure memory controller of the memory device based on the RFID component being activated 440 — Generate a digital signature based on a private key and the device identifier based on the secure memory controller receiving the trigger signal 450 — Transmit a message to the verification system, wherein the message includes the digital signature and the device identifier 460 — Look up a public key associated with the private key using the device identifier received from the RFID component, the public key being stored in a database of the verification system 470 — Authenticate the memory device based on the message received from the communication interface and the public key retrieved from the database

FIG. 4

MANAGED MEMORY DEVICE WITH INTEGRATED RADIO-FREQUENCY IDENTIFICATION COMPONENT FOR CRYPTOGRAPHIC TRACKING

TECHNICAL FIELD

The present disclosure generally relates to memory devices, memory device operations, and, for example, to a managed memory device with an integrated radio-frequency identification (RFID) component for cryptographic tracking.

BACKGROUND

A non-volatile memory device, such as a NAND memory device, may use circuitry to enable electrically programming, erasing, and storing of data even when a power source is not supplied. Non-volatile memory (NVM) or non-volatile storage is a type of computer memory that can retain stored information even after power is removed. Thus, NVM is used for long-term persistent storage of data. Non-volatile memory devices may be used in various types of electronic devices, such as computers, mobile phones, or electronic medication boxes, among other examples.

An electronic medication box, also known as a smart pill box, is a battery-powered device that uses technology to help patients take their medication and track their adherence. Some electronic medication boxes can also notify a patient's healthcare provider if a dose is missed. Thus, an electronic medication box may include compartments for storing and/ or dispensing one or more types of medication. Each compartment may be accessible by a respective lid. An electronic medication box may include NVM for storing data related to the one or more types of medications and/or patient information. An electronic medication box may record when each lid is opened and closed. An electronic medication box may also issue reminder alarms with visual and/or auditory components to remind a patient when to take their medication.

BRIEF DESCRIPTION OF THE DRAWINGS

FIG. 4 is a flowchart of an example method associated with a managed memory device with an integrated radio-frequency identification component for cryptographic tracking.

DETAILED DESCRIPTION

Figure 1:
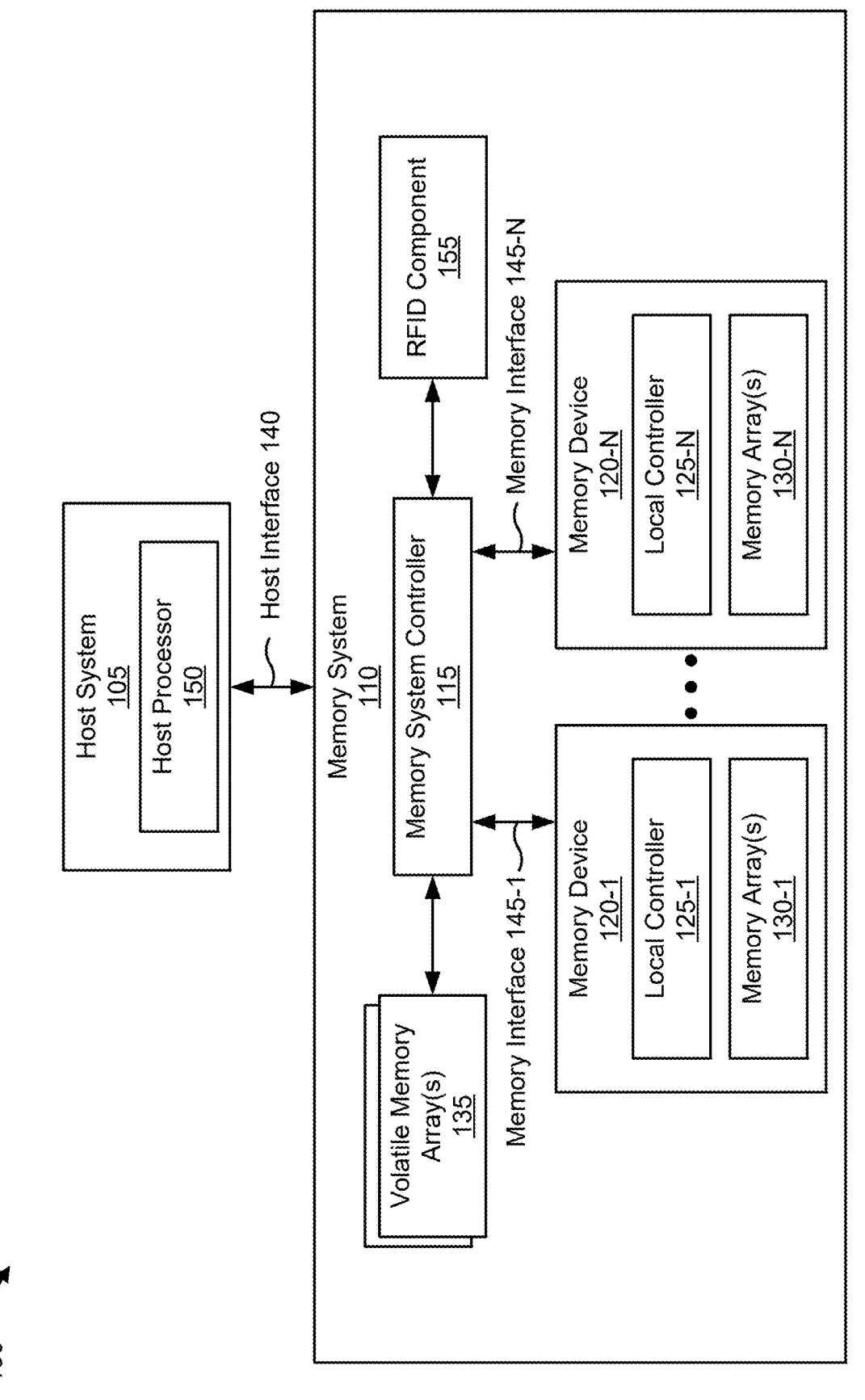
FIG. 1 is a diagram illustrating an example system capable of managed memory device with an integrated radio-frequency identification component for cryptographic tracking.

The pharmaceutical industry faces critical challenges in ensuring medication traceability, combating counterfeiting, and managing a complex supply chain. Currently there is no way to automatically track how many products have been consumed, disposed of, or given to third parties (e.g., charities, pharmacies, or doctors), or recycled. Additionally, tracking medications or electronic medication boxes can be labor intensive and susceptible to human error. Moreover, different countries have different rules for regulating how medications should be handled. Moreover, electronic medication boxes may store patient-sensitive information that is vulnerable to cyberattacks. Current systems fail to provide a secure, efficient, and automated method to oversee and track medication distribution from production to patient to disposal.

Some implementations described herein provide a secure and automated system to enhance traceability and authenticity in pharmaceutical distribution. For example, an electronic medication box that includes a managed memory device with an integrated RFID component may be configured for cryptographic tracking and authentication. The electronic medication box may be linked with one or more medical prescriptions and may be used in a distribution of pharmaceuticals and synchronized with the entire supply chain from a manufacturer, to a local distributor, to a pharmacy, to a patient, and to the care and disposal of the product itself.

A cryptographic tracking system may link the RFID component to the managed memory device, allowing each entity within the supply chain to verify the authenticity of the managed memory device. The managed memory device may include one or more NVM dies (e.g., NAND memory dies) and a memory controller that manages or is otherwise integrated with the one or more NVM dies. An integration of the RFID component, the memory controller, and the one or more NVM dies into a managed memory device (e.g., into a single package) may provide maximum security. For example, the memory controller may be configured to add a cryptographic signature to the managed memory device, preventing data stored in the one or more NVM dies from being exposed to an attacker. A public cryptographic key may be used to verify the cryptographic signature and to certify, prior to exchanging sensitive information with the managed memory device, that the managed memory device (e.g., the electronic medication box) is authentic and linked to a particular user or patient.

A tracking system may include a verification system with a database that stores a public key paired with a corresponding private key, and a host terminal configured to store data related to a user profile. The host terminal may also log tracking information each time the managed memory device is successfully authenticated. Moreover, the tracking system may operate such that the user profile is linked to the managed memory device, enabling the verification system to tailor the transmission of specific data to the managed memory device based on the user profile. The utilization of electronic medication boxes with integrated RFID and memory technology may serve to facilitate an enhanced level of traceability throughout the medical supply chain, encompassing inventory management, automated pharmacy dispensing, and patient safety protocols through real-time informational updates and alerts.

The technical benefits of the tracking system may include a reinforced security posture ensured by the memory controller's cryptographic functions, which prevent unauthorized access to sensitive health data, thereby upholding stringent data privacy standards. Additionally, the tracking system promotes environmental sustainability by mitigating the reliance on paper-based documentation, effectively conserving paper resources. The incorporation of real-time updates through this tracking system ensures accuracy of medical information, thereby conserving network resources and processing resources by streamlining communication channels and reducing the likelihood of errors associated with outdated data. By addressing these technical challenges, the tracking system provides a robust, secure, and resource-efficient approach to medication distribution and management within healthcare environments.

While some implementations may be directed to electronic medication boxes, the managed memory device may be implemented in any device that is associated with a specific user and in which tracking, secure data management, and authentication is desired. Thus, the tracking system may be related to tracking and authenticating the managed memory device, and securely communicating with the managed memory device.

FIG. 1 is a diagram illustrating an example system 100 capable of managed memory device with an integrated radio-frequency identification component for cryptographic tracking. The system 100 may include one or more devices, apparatuses, and/or components for performing operations described herein. For example, the system 100 may include a host system 105 and a memory system 110. The memory system 110 may include a memory system controller 115 and one or more memory devices 120, shown as memory devices 120-1 through 120-N (where N≥1). A memory device may include a local controller 125 and one or more memory arrays 130. The host system 105 may communicate with the memory system 110 (e.g., the memory system controller 115 of the memory system 110) via a communication interface 140. The memory system controller 115 and the memory devices 120 may communicate via respective memory interfaces 145, shown as memory interfaces 145-1 through 145-N (where N≥1).

The system 100 may be any electronic device configured to store data in memory. For example, the system 100 may be a computer, a mobile phone, a wired or wireless communication device, a network device, a server, a device in a data center, a device in a cloud computing environment, a vehicle (e.g., an automobile or an airplane), and/or an Internet of Things (IoT) device. The host system 105 may include a host processor 150. The host processor 150 may include one or more processors configured to execute instructions and store data in the memory system 110. For example, the host processor 150 may include a central processing unit (CPU), a graphics processing unit (GPU), a field-programmable gate array (FPGA), an application-specific integrated circuit (ASIC), and/or another type of processing component.

The memory system 110 may be any electronic device or apparatus configured to store data in memory. For example, the memory system 110 may be a hard drive, a solid-state drive (SSD), a flash memory system (e.g., a NAND flash memory system or a NOR flash memory system), a universal serial bus (USB) drive, a memory card (e.g., a secure digital (SD) card), a secondary storage device, a non-volatile memory express (NVMe) device, an embedded multimedia card (eMMC) device, a dual in-line memory module (DIMM), and/or a random-access memory (RAM) device, such as a dynamic RAM (DRAM) device or a static RAM (SRAM) device.

The memory system controller 115 may be any device configured to control operations of the memory system 110 and/or operations of the memory devices 120. For example, the memory system controller 115 may include control logic, a memory controller, a system controller, an ASIC, an FPGA, a processor, a microcontroller, and/or one or more processing components. In some implementations, the memory system controller 115 may communicate with the host system 105 and may instruct one or more memory devices 120 regarding memory operations to be performed by those one or more memory devices 120 based on one or more instructions from the host system 105. For example, the memory system controller 115 may provide instructions to a local controller 125 regarding memory operations to be performed by the local controller 125 in connection with a corresponding memory device 120.

A memory device 120 may include a local controller 125 and one or more memory arrays 130. In some implementations, a memory device 120 includes a single memory array 130. In some implementations, each memory device 120 of the memory system 110 may be implemented in a separate semiconductor package or on a separate die that includes a respective local controller 125 and a respective memory array 130 of that memory device 120. The memory system 110 may include multiple memory devices 120 (e.g., multiple memory dies).

A local controller 125 may be any device configured to control memory operations of a memory device 120 within which the local controller 125 is included (e.g., and not to control memory operations of other memory devices 120). For example, the local controller 125 may include control logic, a memory controller, a system controller, an ASIC, an FPGA, a processor, a microcontroller, and/or one or more processing components. In some implementations, the local controller 125 may communicate with the memory system controller 115 and may control operations performed on a memory array 130 coupled with the local controller 125 based on one or more instructions from the memory system controller 115. As an example, the memory system controller 115 may be an SSD controller, and the local controller 125 may be a NAND controller. The memory system controller 115 may be a secure memory controller configured with a cryptographic function for generating, based on asymmetric encryption, a digital signature using a private key. The memory system controller 115 may include a physical unclonable function (PUF) configured to generate at least one of a private key or a device identifier of the memory system 110.

Thus, the memory system 110 may be a managed memory device, such as a managed NAND device. A managed memory device is a memory device that includes one or more memory dies, a memory controller, and a management firmware that supports and facilitates an integration between the one or more memory dies and the memory controller. The memory controller may be a secure memory controller configured to manage operations of the one or more memory dies. Additionally, the secure memory controller may be configured with a cryptographic function for generating a digital signature based on asymmetric encryption. It is possible to increase a storage density of the managed memory device by vertically stacking two or more memory dies to form a die stack or memory stack. Stacked NAND memory may allow large amounts of data to be stored in a relatively small physical space, improving the efficiency and storage capacity of devices. However, memory dies may also be distributed laterally on a substrate. In some implementations, multiple die stacks may be provided.

A memory array 130 may include an array of memory cells configured to store data. For example, a memory array 130 may include a non-volatile memory array (e.g., a NAND memory array or a NOR memory array) or a volatile memory array (e.g., an SRAM array or a DRAM array). In some implementations, the memory system 110 may include one or more volatile memory arrays 135. A volatile memory array 135 may include an SRAM array and/or a DRAM array, among other examples. The one or more volatile memory arrays 135 may be included in the memory system controller 115, in one or more memory devices 120, and/or in both the memory system controller 115 and one or more memory devices 120. In some implementations, the memory system 110 may include both non-volatile memory capable of maintaining stored data after the memory system 110 is powered off and volatile memory (e.g., a volatile memory array 135) that requires power to maintain stored data and that loses stored data after the memory system 110 is powered off. For example, a volatile memory array 135 may cache data read from or to be written to non-volatile memory, and/or may cache instructions to be executed by a controller of the memory system 110.

The communication interface 140 enables communication between the host system 105 (e.g., the host processor 150) and the memory system 110 (e.g., the memory system controller 115). The communication interface 140 may include, for example, a Small Computer System Interface (SCSI), a Serial-Attached SCSI (SAS), a Serial Advanced Technology Attachment (SATA) interface, a Peripheral Component Interconnect Express (PCIe) interface, an NVMe interface, a USB interface, a Universal Flash Storage (UFS) interface, an eMMC interface, a double data rate (DDR) interface, a DIMM interface, or a wireless interface, such as Bluetooth, near-field communication, or Wi-Fi.

The memory interface 145 enables communication between the memory system 110 and the memory device 120. The memory interface 145 may include a non-volatile memory interface (e.g., for communicating with non-volatile memory), such as a NAND interface or a NOR interface. Additionally, or alternatively, the memory interface 145 may include a volatile memory interface (e.g., for communicating with volatile memory), such as a DDR interface.

Although the example memory system 110 described above includes a memory system controller 115, in some implementations, the memory system 110 does not include a memory system controller 115. For example, an external controller (e.g., included in the host system 105) and/or one or more local controllers 125 included in one or more corresponding memory devices 120 may perform the operations described herein as being performed by the memory system controller 115. Furthermore, as used herein, a "memory controller" may refer to the memory system controller 115 or a local controller 125. In some implementations, a set of operations described herein as being performed by a controller may be performed by a single controller. For example, the entire set of operations may be performed by a single memory system controller 115 or a single local controller 125. Alternatively, a set of operations described herein as being performed by a controller may be performed by more than one controller. For example, a first subset of the operations may be performed by the memory system controller 115 and a second subset of the operations may be performed by a local controller 125. Furthermore, the term "memory apparatus" may refer to the memory system 110 or a memory device 120, depending on the context.

A controller (e.g., the memory system controller 115 or a local controller 125) may control operations performed on memory (e.g., a memory array 130), such as by executing one or more instructions and/or controlling access to a memory array 130. For example, the memory system 110 and/or a memory device 120 may store one or more instructions in memory as firmware, and the controller may execute those one or more instructions. Additionally, or alternatively, the controller may receive one or more instructions from the host system 105 and/or from the memory system controller 115, and may execute those one or more instructions. In some implementations, a non-transitory computer-readable medium (e.g., volatile memory and/or non-volatile memory)

may store a set of instructions (e.g., one or more instructions or code) for execution by the controller. The controller may execute the set of instructions to perform one or more operations or methods described herein. In some implementations, execution of the set of instructions, by the controller, causes the controller, the memory system 110, and/or a memory device 120 to perform one or more operations or methods described herein. In some implementations, hardwired circuitry is used instead of or in combination with the one or more instructions to perform one or more operations or methods described herein. Additionally, or alternatively, the controller may be configured to perform one or more operations or methods described herein. An instruction is sometimes called a "command."

For example, the controller (e.g., the memory system controller 115 or a local controller 125) may transmit signals to and/or receive signals from memory (e.g., one or more memory arrays 130) based on the one or more instructions, such as to transfer data to (e.g., write or program), to transfer data from (e.g., read), to erase, and/or to refresh all or a portion of the memory (e.g., one or more memory cells, pages, sub-blocks, blocks, or planes of the memory). Additionally, or alternatively, the controller may be configured to control access to the memory and/or to provide a translation layer between the host system 105 and the memory (e.g., for mapping logical addresses to physical addresses of a memory array 130). In some implementations, the controller may translate a host interface command (e.g., a command received from the host system 105) into a memory interface command (e.g., a command for performing an operation on a memory array 130).

The memory system 110 may include an RFID component 155. The RFID component 155 may include a radio transponder called a tag, a radio receiver, and a transmitter. When triggered by an electromagnetic interrogation pulse from a nearby RFID reader device, the tag may transmit digital data, for instance a device identifier or inventory number, back to the RFID reader device or to any other electronic device communicatively coupled to the RFID component 155. In some implementations, the RFID component 155 may be part of or coupled to the communication interface 140. The RFID component 155 may be communicatively coupled to the memory system controller 115. For example, based on being activated by the RFID reader device, provide a trigger signal to the memory system controller 115 and transmit the device identifier to the RFID reader device. The RFID component 155 may receive the device identifier from the memory system controller 115. For example, the PUF of the memory system controller 115 may generate the device identifier and provide the device identifier to the RFID component 155.

In some implementations, the memory system 110 may be an electronic medication box that includes one or more compartments for storing medication; an RFID component configured to communicate with an external system (e.g., host system 105) for transmitting a device identifier to the external system and for receiving medical data from the external system; one or more memory dies configured to store the medical data; a communication interface configured to transmit a message that includes a digital signature and the device identifier for authenticating the electronic medication box; and a secure memory controller configured to manage operations of the one or more memory dies, wherein the secure memory controller is configured with a cryptographic function for generating the digital signature based on asymmetric encryption, wherein the RFID component is configured to provide a trigger signal to the secure memory controller based on the RFID component being activated by the external system, and wherein the secure memory controller is configured to generate the digital signature for being provided in the message based on the secure memory controller receiving the trigger signal.

In some implementations, the system 100 may be a cryptographic tracking system that includes a verification system and a memory device (e.g., memory system 110). The verification system may include an RFID communication device; a database configured to store a public key associated with a private key; and a host terminal configured to store data associated with a user profile. The memory device may include an RFID component configured to communicate with the RFID communication device for transmitting a device identifier to the RFID communication device and for receiving the data from the RFID communication device; one or more memory dies configured to store the data received from the RFID communication device; a communication interface configured to transmit a message that includes a digital signature and the device identifier for authenticating the memory device; and a secure memory controller configured to manage operations of the one or more memory dies. The secure memory controller is configured with a cryptographic function for generating, based on asymmetric encryption, the digital signature using the private key. The RFID component is configured to, based on being activated by the RFID communication device, provide a trigger signal to the secure memory controller and transmit the device identifier to the RFID communication device. The secure memory controller is configured to, based on receiving the trigger signal, generate the digital signature for being provided in the message. The host terminal is configured to look up the public key in the database based on the device identifier received by the RFID communication device. The host terminal is configured to authenticate the memory device based on the message received from the communication interface and the public key retrieved from the database. The host system 105 may be part of the verification system. For example, the host system 105 may include the RFID communication device, the database, and/or the host terminal.

In some implementations, one or more systems, devices, apparatuses, components, and/or controllers of FIG. 1 may be configured to activate an RFID component of a memory device; transmit a device identifier of the memory device to the verification system based on the RFID component being activated; transmit a trigger signal to a secure memory controller of the memory device based on the RFID component being activated; generate a digital signature based on a private key and the device identifier based on the secure memory controller receiving the trigger signal; transmit a message to the verification system, wherein the message includes the digital signature and the device identifier; look up a public key associated with the private key using the device identifier received from the RFID component, the public key being stored in a database of the verification system; and authenticate the memory device based on the message received from the communication interface and the public key retrieved from the database.

The number and arrangement of components shown in FIG. 1 are provided as an example. In practice, there may be additional components, fewer components, different components, or differently arranged components than those shown in FIG. 1. Furthermore, two or more components shown in FIG. 1 may be implemented within a single component, or a single component shown in FIG. 1 may be implemented as multiple, distributed components. Additionally, or alternatively, a set of components (e.g., one or more components) shown in FIG. 1 may perform one or more operations described as being performed by another set of components shown in FIG. 1.

Figure 2:
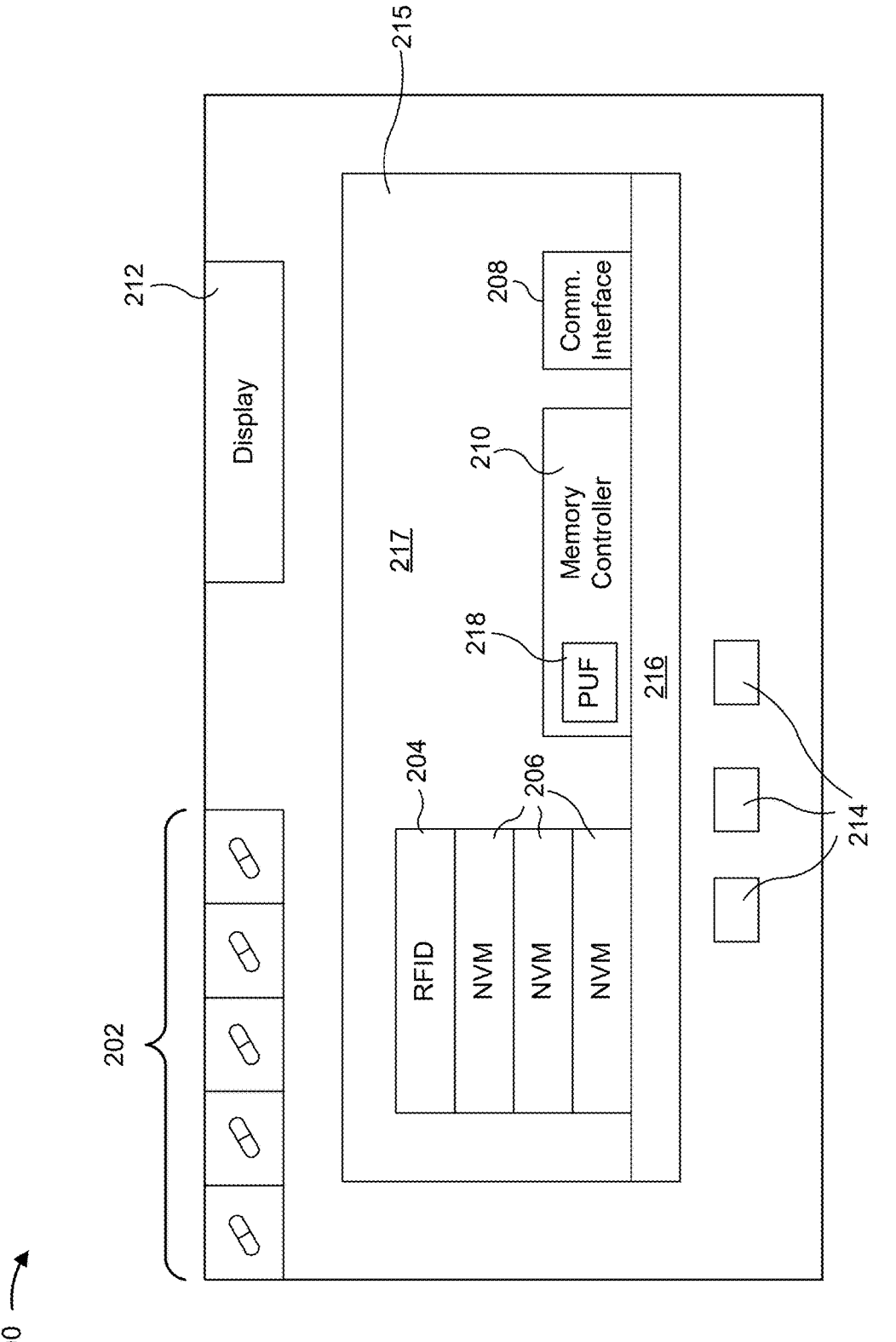
FIG. 2 shows an electronic medication box according to one or more examples.

FIG. 2 shows an electronic medication box 200 according to one or more examples. The electronic medication box 200 may include the memory system 110 described in connection with FIG. 1. The electronic medication box 200 may include one or more compartments 202 for storing medication, an RFID component 204, one or more memory dies 206, a communication interface 208, a secure memory controller 210, a display 212, and one or more input components 214. The RFID component 204, the memory dies 206, the communication interface 208, and the secure memory controller 210 may be integrated into a single memory apparatus, such as a packaged memory device 215 that includes a logic substrate 216 and a housing 217.

The memory dies 206 may be NVM dies, such as NAND memory dies. The memory dies 206 may be arranged in a vertical stack. The RFID component 204 may also be arranged in the vertical stack, for example, on top of the memory dies 206. Components of the vertical stack may be connected with through-silicon vias (TSVs).

The secure memory controller 210 may be a memory controller (e.g., memory system controller 115) that is configured to manage operations of the memory dies 206, and may be configured with a cryptographic function for generating a digital signature based on asymmetric encryption. In addition, the secure memory controller 210 may include a PUF 218 that is configured to generate at least one of a private key or a device identifier that is unique to the electronic medication box 200. The communication interface 208 may be a host interface, similar to host interface 140 described in connection with FIG. 1. In some implementations, the communication interface 208 may be arranged external to the memory device 215 while still being integrated within the electronic medication box 200. The communication interface 208 may be communicatively coupled to the secure memory controller 210.

The RFID component 204 may communicate with an external system for transmitting the device identifier to the external system. The RFID component 204 may also receive, from the external system, medical data corresponding to a user (e.g., to a patient) of the electronic medication box 200.

The communication interface 208 may transmit a message that includes the digital signature and the device identifier for authenticating the electronic medication box 200. For example, the communication interface 208 may transmit the message to the external system for authentication and device tracking. The RFID component 204 may enable real-time tracking of the electronic medication box 200.

The RFID component 204 may provide a trigger signal to the secure memory controller 210 based on the RFID component 204 being activated by the external system. The secure memory controller 210 may generate the digital signature, for being provided in the message, based on the secure memory controller 210 receiving the trigger signal. Thus, when the RFID component 204 is activated by an RFID reader device, the RFID component 204 may send the trigger signal to the secure memory controller 210 to initiate an authentication of the electronic medication box 200. The secure memory controller 210 may generate the digital signature using the private key and the device identifier, and provide the digital signature and the device identifier to the communication interface 208. The communication interface 208 may generate the message, which may include the digital signature and the device identifier.

In addition, the PUF 218 may generate the device identifier and provide the device identifier to the RFID component 204 for transmitting the device identifier to the RFID reader device. The PUF 218 may be implemented in logic in the secure memory controller 210 or may be embedded in DRAM.

The secure memory controller 210 may be an input/output (I/O) controller that controls data being read from the memory dies 206 and/or being written to the memory dies 206. For example, the secure memory controller 210 may grant read/write access to the memory dies 206 based on the electronic medication box 200 being successfully authenticated by the external system. Thus, user-sensitive data may be protected.

In some implementations, the device identifier is linked to a patient profile of a patient that is assigned to the electronic medication box 200, and the medical data corresponds to information associated with the patient profile. For example, the electronic medication box 200 may be linked to one or more medical prescriptions included in the patient profile. In some implementations, the medical data includes a medication datasheet associated with the medication.

The electronic medication box 200 may store times at which medication is to be taken by the patient according to the patient profile. The electronic medication box 200 may be configured to provide alerts to the user. For example, the electronic medication box 200 may alert the user that it is time to take their medication. This can be through audible alerts, flashing lights, or notifications sent to a smartphone. The electronic medication box 200 may automatically log patient medication intake in the memory dies 206 each time the patient opens a compartment 202 box to take a medication. The electronic medication box 200 may also generate an alert when medication is not taken at a prescribed time. The electronic medication box 200 may also generate an alert when medication has expired.

The electronic medication box 200 may receive and store medication datasheets corresponding to the patient profile and to the medication linked to the patient profile that is assigned to the electronic medication box 200. The datasheets may be in a language specified in the patient profile. In addition, the electronic medication box 200 may be programmed according to country rules and regulations based on the patient profile (e.g., based on a residence of the patient). the electronic medication box 200 may store the datasheets and other medical data corresponding to information associated with the patient profile in the memory dies 206. The medical data may be protected based on the asymmetric encryption provided by the secure memory controller 210. Certain medical data, such as datasheets, may be updated or overwritten by an authorized external system, which may validate the electronic medication box 200 prior to accessing the medical data stored on the memory dies 206.

In some implementations, datasheets may be accessed from any Internet-connected device, such as a smartphone, tablet, or computer. Search functions may be used to quickly find specific information. Datasheets may be updated in real-time as changes to datasheets are made to ensure the information is current.

As indicated above, FIG. 2 is provided as an example. Other examples may differ from what is described with regard to FIG. 2.

Figure 3:
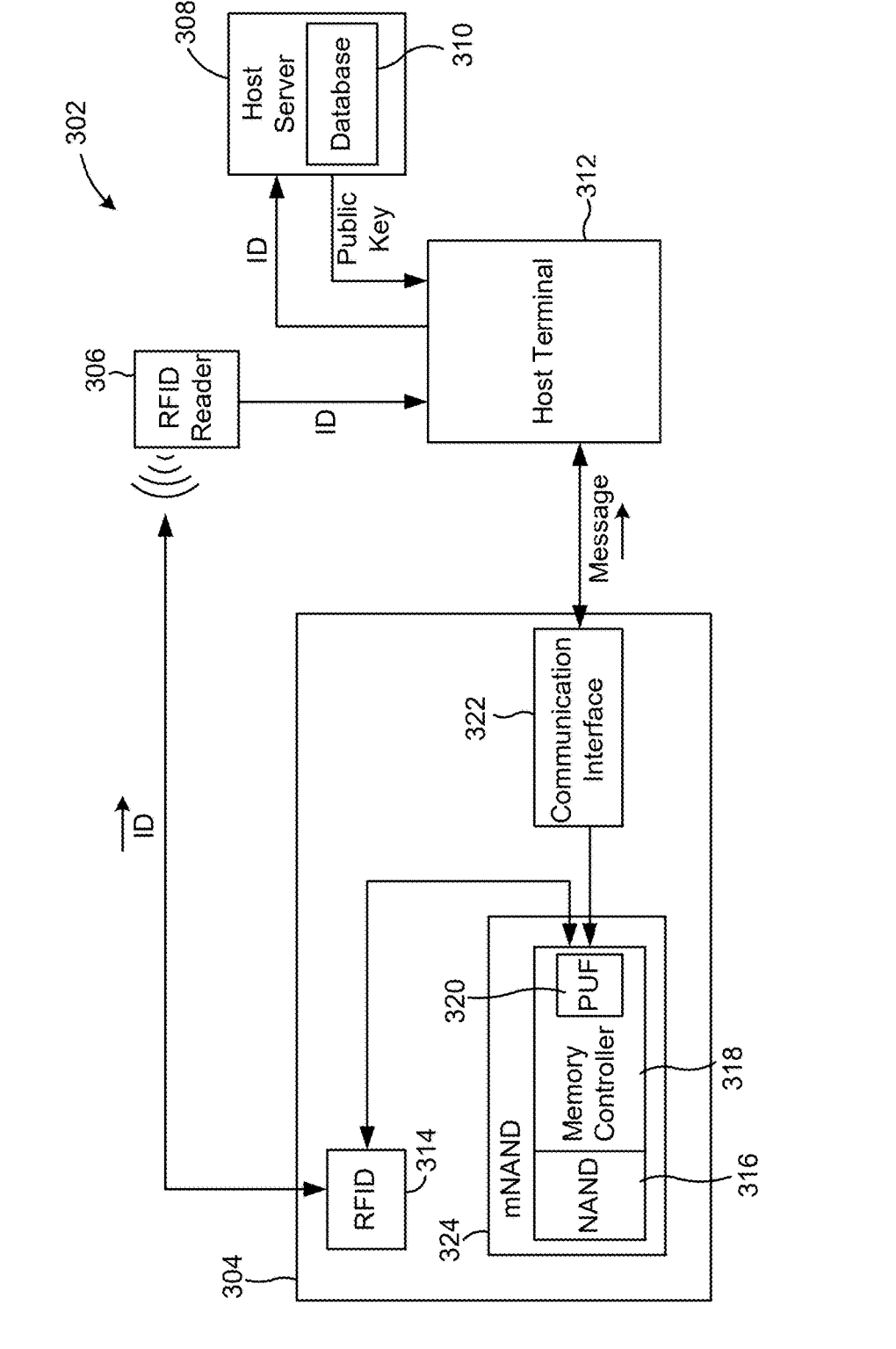
FIG. 3 shows a cryptographic tracking system according to one or more examples.

FIG. 3 shows a cryptographic tracking system 300 according to one or more examples. The cryptographic tracking system 300 may include the memory system 110 described in connection with FIG. 1 or the electronic medication box 200 described in connection with FIG. 2.

The cryptographic tracking system 300 may include a verification system 302 and a memory device 304. The verification system 302 may include an RFID communication device 306 (e.g., an RFID reader device), a host server 308 that includes a database 310 configured to store a public key associated with a private key, and a host terminal 312 configured to store data associated with a user profile (e.g., a patient profile). The host terminal 312 may be similar to the host system 105 described in connection with FIG. 1.

The memory device 304 may include an RFID component 314, one or more memory dies 316, a secure memory controller 318 with a PUF 320, and a communication interface 322. The memory dies 316 and the secure memory controller 318 may be integrated in a managed memory device 324. Thus, the memory device 304 may be similar to or may be incorporated in the memory system 110 described in connection with FIG. 1 or the electronic medication box 200 described in connection with FIG. 2. In some implementations, the managed memory device 324 may be a managed NAND (mNAND) device, and the memory dies 316 may be NAND memory dies. The secure memory controller 318 may correspond to memory system controller 115 or a local controller 125, described in connection with FIG. 1.

The RFID component 314 may communicate with the RFID communication device 306 for transmitting a device identifier ID to the RFID communication device 306 and for receiving data from the RFID communication device 306. The memory dies 316 may store data received from the RFID communication device 306 and/or received by the communication interface 322 from the host terminal 312. The communication interface 322 may transmit a message that includes a digital signature and the device identifier for authenticating the memory device 304. The secure memory controller 318 may manage operations of the memory dies 316, and may be configured with a cryptographic function for generating, based on asymmetric encryption, the digital signature using the private key.

The RFID component 314 may, based on being activated by the RFID communication device 306, provide a trigger signal to the secure memory controller 318 and transmit the device identifier ID to the RFID communication device 306. The secure memory controller 318 may, based on receiving the trigger signal, generate the digital signature for being provided in the message. The secure memory controller 318 may be provided to the communication interface 322 for being incorporated into the message. The communication interface 322 may transmit the message to the host terminal 312. The host terminal 312 may receive the device identifier ID from the RFID communication device 306, and may receive the message from the communication interface 322. The host terminal 312 may look up the public key in the database 310 based on the device identifier ID received by the RFID communication device 306. Assuming the device identifier ID is matched with a public key in the database 310, the host server 308 may provide the public key to the host terminal 312. On the other hand, if the device identifier ID is not matched with a public key in the database 310, the host server 308 indicates an error to the host terminal 312, indicating that authentication of the memory device 304 has failed.

In response to receiving the public key from the host server 308, the host terminal 312 may authenticate the memory device 304 based on the message received from the communication interface 322 and the public key retrieved from the database 310. For example, the host terminal 312 may authenticate the message using the public key retrieved from the database 310 (e.g., based on asymmetric encryption/decryption). For example, the host terminal 312 may authenticate the memory device 304 based on the digital signature, the device identifier ID received in the message, and the public key retrieved from the database 310. If the host terminal 312 successfully authenticated the message using the public key retrieved from the database 310, the host terminal 312 may indicate that the memory device 304 is validated and authentic. However, if the authentication fails, the host terminal 312 may indicate that the message has been compromised or that the memory device 304 is invalid. The host terminal 312 may transmit data to the memory device 304 based on the memory device 304 being successfully authenticated. In addition, the host terminal 312 may log tracking information into the user profile and/or the database 310 based on the memory device 304 being successfully authenticated. The host terminal 312 may generate the tracking information associated with the memory device 304 based on the memory device 304 being successfully authenticated. The tracking information may include the device identifier ID, a location of the host terminal 312, and a time stamp of when the memory device 304 was successfully authenticated. Thus, the memory device 304 may be tracked by the verification system 302.

In some implementations, the user profile may be linked to the memory device 304, and the host terminal 312 may select data for transmission to the memory device 304 based on the user profile. For example, the data may include medical data associated with a medication and the user profile, including medication datasheets, dosage information, and/or times or frequency to administer medication. In some implementations, the host terminal 312 may be a pharmacy terminal. In addition, the device identifier ID may be linked to the user profile to which the memory device 304 is assigned. Thus, the data (e.g., medical data) may correspond to information associated with the user profile. In some implementations, the host terminal 312 may transmit and the communication interface 322 may receive at least one of alerts, updates, or control signals from the host terminal 312.

Integrating the memory device 304, that contains an integration between the RFID component 314 and the managed memory device 324 that is implemented with a cryptographic tracking system that links an RFID to the managed memory device 324, into an electronic medication box may provide one or more benefits, including full traceability of medication throughout an entire medication supply chain; integration of the medication datasheet into the electronic medication box, with multi-language support; aid a patient with managing taking the medication, including providing reminder alerts for taking the medication, or when a dose has been missed; support a process of returning the medication to a pharmacy in the event that the medical treatment is completed, or in case the an expiration date of the medication has lapsed; facilitate a supply chain process; and provide new functionalities covering the entire medication supply chain. The usage of the integrated asymmetric encryption ensures that private health data will be not accessible to unauthorized users, thus providing a secure privacy level to the data stored in the memory device 304.

As indicated above, FIG. 3 is provided as an example. Other examples may differ from what is described with regard to FIG. 3.

FIG. 4 is a flowchart of an example method 400 associated with a managed memory device with an integrated radio-frequency identification component for cryptographic tracking. In some implementations, a cryptographic tracking system (e.g., the cryptographic tracking system 300) may perform or may be configured to perform the method 400. In some implementations, another device or a group of devices separate from or including the cryptographic tracking system may perform or may be configured to perform the method 400. Additionally, or alternatively, one or more components of the cryptographic tracking system (e.g., verification system 302 and/or memory device 304) may perform or may be configured to perform the method 400. Thus, means for performing the method 400 may include the cryptographic tracking system and/or one or more components of the cryptographic tracking system. Additionally, or alternatively, a non-transitory computer-readable medium may store one or more instructions that, when executed by the cryptographic tracking system, cause the cryptographic tracking system to perform the method 400.

As shown in FIG. 4, the method 400 may include activating an RFID component of a memory device (block 410). As further shown in FIG. 4, the method 400 may include transmitting a device identifier of the memory device to the verification system based on the RFID component being activated (block 420). As further shown in FIG. 4, the method 400 may include transmitting a trigger signal to a secure memory controller of the memory device based on the RFID component being activated (block 430). As further shown in FIG. 4, the method 400 may include generating a digital signature based on a private key and the device identifier based on the secure memory controller receiving the trigger signal (block 440). As further shown in FIG. 4, the method 400 may include transmitting a message to the verification system, wherein the message includes the digital signature and the device identifier (block 450). As further shown in FIG. 4, the method 400 may include looking up a public key associated with the private key using the device identifier received from the RFID component, the public key being stored in a database of the verification system (block 460). As further shown in FIG. 4, the method 400 may include authenticating the memory device based on the message received from the communication interface and the public key retrieved from the database (block 470).

The method 400 may include additional aspects, such as any single aspect or any combination of aspects described below and/or described in connection with one or more other methods or operations described elsewhere herein.

In a first aspect, authenticating the memory device is based on the digital signature, the device identifier received in the message, and the public key retrieved from the database.

In a second aspect, alone or in combination with the first aspect, the method 400 includes transmitting, by the verification system, data to the memory device based on the memory device being successfully authenticated.

In a third aspect, alone or in combination with one or more of the first and second aspects, the method 400 includes linking a user profile to the memory device, and selecting, by the verification system, the data for transmission to the memory device based on the user profile.

In a fourth aspect, alone or in combination with one or more of the first through third aspects, the memory device is an electronic medication box configured to store medication, and wherein the data is medical data associated with the medication and the user profile.

In a fifth aspect, alone or in combination with one or more of the first through fourth aspects, the method 400 includes generating, by the verification system, tracking information associated with the memory device based on the memory device being successfully authenticated.

Although FIG. 4 shows example blocks of a method 400, in some implementations, the method 400 may include additional blocks, fewer blocks, different blocks, or differently arranged blocks than those depicted in FIG. 4. Additionally, or alternatively, two or more of the blocks of the method 400 may be performed in parallel. The method 400 is an example of one method that may be performed by one or more devices described herein. These one or more devices may perform or may be configured to perform one or more other methods based on operations described herein.

In some implementations, an electronic medication box includes one or more compartments for storing medication; an RFID component configured to communicate with an external system for transmitting a device identifier to the external system and for receiving medical data from the external system; one or more memory dies configured to store the medical data; a communication interface configured to transmit a message that includes a digital signature and the device identifier for authenticating the electronic medication box; and a secure memory controller configured to manage operations of the one or more memory dies, wherein the secure memory controller is configured with a cryptographic function for generating the digital signature based on asymmetric encryption, wherein the RFID component is configured to provide a trigger signal to the secure memory controller based on the RFID component being activated by the external system, and wherein the secure memory controller is configured to generate the digital signature, for being provided in the message, based on the secure memory controller receiving the trigger signal.

In some implementations, a cryptographic tracking system, comprising: a verification system, comprising; an RFID communication device; a database configured to store a public key associated with a private key; and a host terminal configured to store data associated with a user profile; and a memory device, comprising: an RFID component configured to communicate with the RFID communication device for transmitting a device identifier to the RFID communication device and for receiving the data from the RFID communication device; one or more memory dies configured to store the data received from the RFID communication device; a communication interface configured to transmit a message that includes a digital signature and the device identifier for authenticating the memory device; and a secure memory controller configured to manage operations of the one or more memory dies, wherein the secure memory controller is configured with a cryptographic function for generating, based on asymmetric encryption, the digital signature using the private key, wherein the RFID component is configured to, based on being activated by the RFID communication device, provide a trigger signal to the secure memory controller and transmit the device identifier to the RFID communication device, wherein the secure memory controller is configured to, based on receiving the trigger signal, generate the digital signature for being provided in the message, wherein the host terminal is configured to look up the public key in the database based on the device identifier received by the RFID communication device, and wherein the host terminal is configured to authenticate the memory device based on the message received from the communication interface and the public key retrieved from the database.

In some implementations, a method includes activating, by a verification system, an RFID component of a memory device; transmitting, by the RFID component, a device identifier of the memory device to the verification system based on the RFID component being activated; transmitting, by the RFID component, a trigger signal to a secure memory controller of the memory device based on the RFID component being activated; generating, by the secure memory controller, a digital signature based on a private key and the device identifier based on the secure memory controller receiving the trigger signal; transmitting, by a communication interface of the memory device, a message to the verification system, wherein the message includes the digital signature and the device identifier; looking up, by the verification system, a public key associated with the private key using the device identifier received from the RFID component, the public key being stored in a database of the verification system; and authenticating, by the verification system, the memory device based on the message received from the communication interface and the public key retrieved from the database.

In some implementations, a managed memory device includes an RFID component configured to communicate with an external system for transmitting a device identifier to the external system; one or more memory dies configured to store data received from the external system; a communication interface configured to transmit a message that includes a digital signature and the device identifier for authenticating the managed memory device; and a secure memory controller configured to manage operations of the one or more memory dies, wherein the secure memory controller is configured with a cryptographic function for generating the digital signature based on asymmetric encryption, wherein the RFID component is configured to provide a trigger signal to the secure memory controller based on the RFID component being activated by the external system, wherein the secure memory controller is configured to generate the digital signature, for being provided in the message, based on the secure memory controller receiving the trigger signal, and wherein at least one of the RFID component or the communication interface is configured to receive the data from the external system. The RFID component may be integrated with the one or more memory dies. In some cases, the RFID component may be coupled or attached to one or more memory dies. For example, the RFID component and the one or more memory dies may be assembled in a vertical stack (e.g., stacked vertically).

The foregoing disclosure provides illustration and description but is not intended to be exhaustive or to limit the implementations to the precise forms disclosed. Modifications and variations may be made in light of the above disclosure or may be acquired from practice of the implementations described herein.

Even though particular combinations of features are recited in the claims and/or disclosed in the specification, these combinations are not intended to limit the disclosure of implementations described herein. Many of these features may be combined in ways not specifically recited in the claims and/or disclosed in the specification. For example, the disclosure includes each dependent claim in a claim set in combination with every other individual claim in that claim set and every combination of multiple claims in that claim set. As used herein, a phrase referring to "at least one of" a list of items refers to any combination of those items, including single members. As an example, "at least one of: a, b, or c" is intended to cover a, b, c, a+b, a+c, b+c, and a+b+c, as well as any combination with multiples of the same element (e.g., a+a, a+a+a, a+a+b, a+a+c, a+b+b, a+c+c, b+b, b+b+b, b+b+c, c+c, and c+c+c, or any other ordering of a, b, and c).

When "a component" or "one or more components" (or another element, such as "a controller" or "one or more controllers") is described or claimed (within a single claim or across multiple claims) as performing multiple operations or being configured to perform multiple operations, this language is intended to broadly cover a variety of architectures and environments. For example, unless explicitly claimed otherwise (e.g., via the use of "first component" and "second component" or other language that differentiates components in the claims), this language is intended to cover a single component performing or being configured to perform all of the operations, a group of components collectively performing or being configured to perform all of the operations, a first component performing or being configured to perform a first operation and a second component performing or being configured to perform a second operation, or any combination of components performing or being configured to perform the operations. For example, when a claim has the form "one or more components configured to: perform X; perform Y; and perform Z," that claim should be interpreted to mean "one or more components configured to perform X; one or more (possibly different) components configured to perform Y; and one or more (also possibly different) components configured to perform Z."

No element, act, or instruction used herein should be construed as critical or essential unless explicitly described as such. Also, as used herein, the articles "a" and "an" are intended to include one or more items and may be used interchangeably with "one or more." Further, as used herein, the article "the" is intended to include one or more items referenced in connection with the article "the" and may be used interchangeably with "the one or more." Where only one item is intended, the phrase "only one," "single," or similar language is used. Also, as used herein, the terms "has," "have," "having," or the like are intended to be open-ended terms that do not limit an element that they modify (e.g., an element "having" A may also have B). Further, the phrase "based on" is intended to mean "based, at least in part, on" unless explicitly stated otherwise. As used herein, the term "multiple" can be replaced with "a plurality of" and vice versa. Also, as used herein, the term "or" is intended to be inclusive when used in a series and may be used interchangeably with "and/or," unless explicitly stated otherwise (e.g., if used in combination with "either" or "only one of").

What is claimed is:

1. A cryptographic tracking system, comprising;
a verification system, comprising:
a radio-frequency identification (RFID) communication device;
a database configured to store a public key associated with a private key; and
a host terminal configured to store data associated with a user profile; and a memory device, comprising:
an RFID component configured to communicate with the RFID communication device for transmitting a device identifier to the RFID communication device and for receiving the data from the RFID communication device;
one or more memory dies configured to store the data received from the RFID communication device;

a communication interface configured to transmit a message that includes a digital signature and the device identifier for authenticating the memory device; and
a secure memory controller configured to manage operations of the one or more memory dies,
wherein the secure memory controller is configured with a cryptographic function for generating, based on asymmetric encryption, the digital signature using the private key,
wherein the memory device is an electronic medication box configured to store medication,
wherein the data is medical data associated with the medication and the user profile,
wherein the RFID component is configured to, based on being activated by the RFID communication device, provide a trigger signal to the secure memory controller and transmit the device identifier to the RFID communication device,
wherein the secure memory controller is configured to, based on receiving the trigger signal, generate the digital signature for being provided in the message,
wherein the host terminal is configured to look up the public key in the database based on the device identifier received by the RFID communication device, and
wherein the host terminal is configured to authenticate the memory device based on the message received from the communication interface, the digital signature, the device identifier received in the message, and the public key retrieved from the database.

2. The cryptographic tracking system of claim 1, wherein the host terminal is configured to transmit the data to the memory device based on the memory device being successfully authenticated.

3. The cryptographic tracking system of claim 2,
wherein the user profile is linked to the memory device, and
wherein the host terminal is configured to select the data for transmission to the memory device based on the user profile.

4. The cryptographic tracking system of claim 1, wherein the host terminal is configured to generate tracking information associated with the memory device based on the memory device being successfully authenticated.

5. The cryptographic tracking system of claim 1, wherein the host terminal is a pharmacy terminal.

6. The cryptographic tracking system of claim 1, wherein the secure memory controller includes a physical unclonable function (PUF) configured to generate at least one of the private key or the device identifier.

7. The cryptographic tracking system of claim 6, wherein the PUF is configured to generate the device identifier and provide the device identifier to the RFID component.

8. The cryptographic tracking system of claim 1,
wherein the device identifier is linked to the user profile to which the memory device is assigned, and
wherein the data corresponds to information associated with the user profile.

9. The cryptographic tracking system of claim 1, wherein the communication interface is configured to receive at least one of alerts, updates, or control signals from the host terminal.

10. A method, comprising:

transmitting, by a radio-frequency identification (RFID) component of a memory device, a device identifier of the memory device;

receiving, by the RFID component, data associated with a user profile;

storing the data in one or more memory dies;

transmitting, by a communication interface, a message that includes a digital signature and the device identifier for authenticating the memory device; and managing, by a secure memory controller, operations of the one or more memory dies, wherein the secure memory controller is configured with a cryptographic function for generating, based on asymmetric encryption, the digital signature using a private key, wherein the memory device is an electronic medication box configured to store medication, wherein the data is medical data associated with the medication and the user profile, wherein the RFID component is configured to, based on being activated by an RFID communication device, provide a trigger signal to the secure memory controller and transmit the device identifier to the RFID communication device, wherein the secure memory controller is configured to, based on receiving the trigger signal, generate the digital signature for being provided in the message, wherein a host terminal is configured to look up a public key in a database based on the device identifier received by the RFID communication device, and wherein the host terminal is configured to authenticate the memory device based on the message received from the communication interface, the digital signature, the device identifier received in the message, and the public key retrieved from the database.

11. The method of claim 10, wherein the host terminal is configured to transmit the data to the memory device based on the memory device being successfully authenticated.

12. The method of claim 11, wherein the user profile is linked to the memory device, and wherein the host terminal is configured to select the data for transmission to the memory device based on the user profile.

13. The method of claim 10, wherein the host terminal is configured to generate tracking information associated with the memory device based on the memory device being successfully authenticated.

14. The method of claim 10, wherein the host terminal is a pharmacy terminal.

15. The method of claim 10, wherein the secure memory controller includes a physical unclonable function (PUF) configured to generate at least one of the private key or the device identifier.

16. The method of claim 15, wherein the PUF is configured to generate the device identifier and provide the device identifier to the RFID component.

17. The method of claim 10, wherein the device identifier is linked to the user profile to which the memory device is assigned, and wherein the data corresponds to information associated with the user profile.

18. The method of claim 10, wherein the communication interface is configured to receive at least one of alerts, updates, or control signals from the host terminal.

19. A non-transitory computer-readable medium storing a set of instructions, the set of instructions comprising:

one or more instructions that, when executed by one or more processors of a memory device, cause the memory device to:

transmit, by a radio-frequency identification (RFID) component of the memory device, a device identifier of the memory device;

receive, by the RFID component, data associated with a user profile;

store the data in one or more memory dies;

transmit, by a communication interface, a message that includes a digital signature and the device identifier for authenticating the memory device; and manage, by a secure memory controller, operations of the one or more memory dies, wherein the secure memory controller is configured with a cryptographic function for generating, based on asymmetric encryption, the digital signature using a private key, wherein the memory device is an electronic medication box configured to store medication, wherein the data is medical data associated with the medication and the user profile, wherein the RFID component is configured to, based on being activated by an RFID communication device, provide a trigger signal to the secure memory controller and transmit the device identifier to the RFID communication device, wherein the secure memory controller is configured to, based on receiving the trigger signal, generate the digital signature for being provided in the message, wherein a host terminal is configured to look up a public key in a database based on the device identifier received by the RFID communication device, and wherein the host terminal is configured to authenticate the memory device based on the message received from the communication interface, the digital signature, the device identifier received in the message, and the public key retrieved from the database.

20. The non-transitory computer-readable medium of claim 19, wherein the one or more instructions further cause the memory device to transmit the data to the memory device based on the memory device being successfully authenticated.

21. The non-transitory computer-readable medium of claim 20, wherein the user profile is linked to the memory device, and wherein the one or more instructions further cause the memory device to select the data for transmission to the memory device based on the user profile.

22. The non-transitory computer-readable medium of claim 19, wherein the one or more instructions further cause the memory device to generate tracking information associated with the memory device based on the memory device being successfully authenticated.

23. The non-transitory computer-readable medium of claim 19, wherein the host terminal is a pharmacy terminal.

24. The non-transitory computer-readable medium of claim 19, wherein the secure memory controller includes a physical unclonable function (PUF) configured to generate at least one of the private key or the device identifier.

25. The non-transitory computer-readable medium of claim 24, wherein the one or more instructions further cause the memory device to generate the device identifier and provide the device identifier to the RFID component.

26. The non-transitory computer-readable medium of claim 19, wherein the device identifier is linked to the user profile to which the memory device is assigned, and wherein the data corresponds to information associated with the user profile.

27. The non-transitory computer-readable medium of claim 19, wherein the one or more instructions further cause the memory device to receive at least one of alerts, updates, or control signals from the host terminal.

\* \* \* \* \*